Sept. 16, 1952 E. S. BOERNER Plant Pat. 1,130
CHRYSANTHEMUM PLANT
Filed Sept. 28, 1951
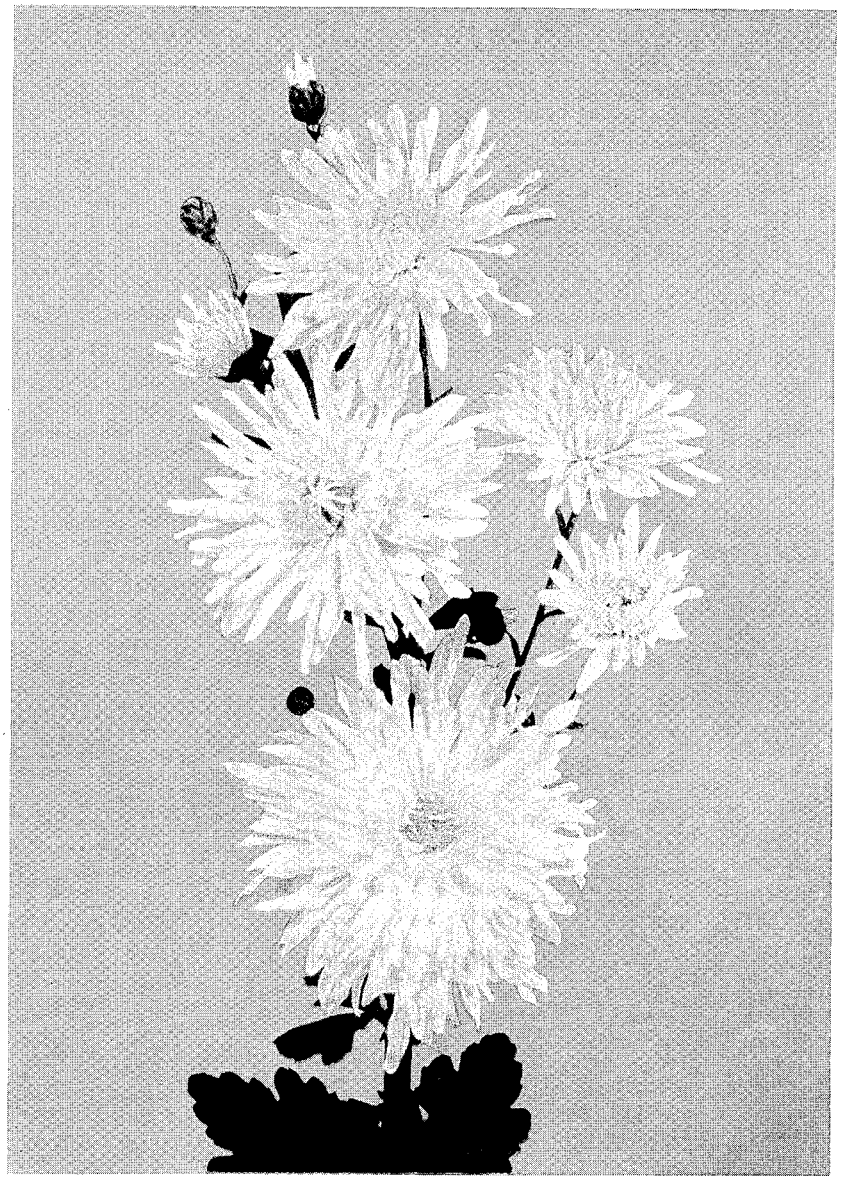
Inventor.
E. S. Boerner
By: Robert Cobb
Attorneys.

Patented Sept. 16, 1952

Plant Pat. 1,130

UNITED STATES PATENT OFFICE 1,130

CHRYSANTHEMUM PLANT

Eugene S. Boerner, Newark, N. Y., assignor to Jackson & Perkins Company, Newark, N. Y., a corporation of New York Application September 28, 1951, Serial No. 248,792

1 Claim. (Cl. 47—60)

The present invention relates to a new and distinct variety of chrysanthemum plant, originated by me by crossing an unnamed and unpatented white seedling with a seedling of "Lavender Lady" × "Pale Moon" (both unpatented).

The primary objective in making this cross was to produce a larger and hardier-flowered outdoor chrysanthemum than has been available heretofore. This objective was fully achieved as the result of the particular cross referred to, as evidenced by the fact that the new variety is endowed with the following characteristics, in a new and unusual combination, which distinguish the new variety from its parents, as well as from all other varieties of its class:

(1) Hardy, decorative type flowers;

(2) Large size white flowers of long-lasting quality;

(3) Graceful appearance and irregular arrangement of the flower petals;

(4) Early-blooming habit; and (5) Freedom of bloom and repetition.

Asexual reproduction of this new variety by top cuttings and by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed in the fields at Newark, New York, in the early afternoon late in the month of September, with color terminology in accordance with Ridgway's Color Standards and Nomenclature:

Parentage: An unnamed white seedling × (a seedling of "Lavender Lady" × "Pale Moon").

Classification: Decorative type.

Growth: Upright and clean; attaining a height of 30 inches.

Cold resistance: Winter hardy in northern New York; flowers burn lightly with early frosts.

Blooming period: Blooms start August 24th and continue until severe freezing in October and November.

Bud:

*Color.*—When sepals first divide—Sea-Foam Green, Plate 31. When petals begin to unfurl—Sea-Foam Yellow, Plate 31. When half blown—inside of petals: White, Plate 53, lightly overcast with Sulphur Yellow, Plate 5; reverse of petals: White, Plate 53.

*Peduncle.*—Color—Cress Green, Plate 31. Strength—medium.

Bloom:

*Size.*—4 to 5 inches.

*Stems.*—Medium size and normal strength.

*Form.*—Decorative type; pistils showing when center fully open.

*Petalage.*—Very double.

*Color.*—Center of flower—Sulphur Yellow, Plate 5. Outer petals—White, Plate 53. Base of petals—Deep Sea-Foam Green, Plate 31. Inside of petals—White, Plate 53. Reverse of petals—White, Plate 53.

*Petals.* — Texture —medium. Form — long; narrow; wavy.

*Fragrance.*—Characteristic chrysanthemum.

Plant:

*Form.*—Upright.

*Growth.*—Vigorous; free.

Foliage:

*Size.*—Small.

*Quantity.*—Normal.

*Color.*—Upper side—Forest Green, Plate 17; reverse side—Light Hellebore Green, Plate 17.

*Texture.*—Leathery.

I claim:

A new and distinct variety of chrysanthemum plant, substantially as herein shown and described, characterized as to novelty by its hardy, decorative type flowers, by the relatively large size of its white flowers of long-lasting quality, by the graceful appearance and irregular arrangement of the flower petals, by its early-blooming habit, and by its freedom of bloom and repetition.

EUGENE S. BOERNER.

No references cited.